United States Patent [19]
Liao et al.

[11] Patent Number: 5,827,525
[45] Date of Patent: Oct. 27, 1998

[54] BUCCAL DELIVERY SYSTEM FOR THERAPEUTIC AGENTS

[75] Inventors: Wei-Chi Liao, Princetion Junction; Agis Kydonieus, Kendall Park; Kishore R. Shah, Bridgewater, all of N.J.

[73] Assignee: Bristol-Myers Squibb Company, Princeton, N.J.

[21] Appl. No.: 711,754

[22] Filed: Sep. 10, 1996

Related U.S. Application Data

[60] Provisional application No. 60/003,600 Sep. 12, 1995.
[51] Int. Cl.$^6$ ........................................ A61F 13/00
[52] U.S. Cl. ........................ 424/435; 424/484; 424/486
[58] Field of Search ....................... 424/449, 448, 424/434, 435, 484, 486; 514/553, 556

[56] References Cited

U.S. PATENT DOCUMENTS

| | | | |
|---|---|---|---|
| 4,538,603 | 9/1985 | Pawelchak et al. | 128/156 |
| 4,551,490 | 11/1985 | Doyle et al. | 524/22 |
| 5,455,043 | 10/1995 | Fischel-Ghodisian | 424/448 |
| 5,607,691 | 3/1997 | Hale | 424/449 |

FOREIGN PATENT DOCUMENTS

0597636A1  5/1994  European Pat. Off. .

OTHER PUBLICATIONS

John D. Smart, "Drug delivery using buccal–adhesive systems", *Advanced Drug Delivery Reviews,* 11 (1993) pp. 253–270.

M. R. Rassing, "Chewing gum as a drug delivery system", *Advanced Drug Delivery Reviews,* 13 (1994) pp. 89–121.

*Primary Examiner*—Thurman K. Page
*Assistant Examiner*—Diedra Faulkner
*Attorney, Agent, or Firm*—Burton Rodney

[57] ABSTRACT

A unidirectional buccal delivery system for the delivery of therapeutic agents over an extended period of time. The delivery system includes a matrix for releasing the drug into the oral cavity at a sustained rate and a means for securing the matrix to the palate or other adequate regions in the oral cavity.

14 Claims, No Drawings

BUCCAL DELIVERY SYSTEM FOR THERAPEUTIC AGENTS

This application is a continuation of Provisional application Ser. No. 60/003,600 filed Sep. 12, 1995.

BRIEF DESCRIPTION OF THE INVENTION

The present invention is directed to a unidirectional buccal delivery system for the delivery of therapeutic agents at a sustained rate over an extended period of time.

DETAILED DESCRIPTION OF THE INVENTION

In accordance with the present invention, a unidirectional buccal delivery system for therapeutic agents is provided.

The term "unidirectional" as used herein is intended to mean that greater than 50%, preferably greater than 80% and most preferably greater than 95% of the drug is released into the buccal cavity and is not absorbed through the mucosa.

The unidirectional delivery system includes a matrix which contains the therapeutic agent for release into the oral cavity. The matrix releases the therapeutic agent at a sustained rate into the oral cavity. The term "sustained rate" as used herein means release of the drug for an extended period of time ranging from about 12 hours to about 7 days.

Preferably the matrix is any hydrophobic or hydrophilic polymeric material. When hydrophilic polymers are used, they should be crosslinked to allow swelling of the matrix, but not dissolution into the oral cavity. The matrix polymer is chosen based on the molecular weight, hydrophobicity or hydrophilicity of the drug and the desired release rate. Thus, for the delivery of a protein, a suitable polymer would be a lightly crosslinked hydrogel which would allow for water absorption and swelling permitting the large hydrophilic protein to be released in the oral cavity. In general, hydrophobic polymers would be chosen to release hydrophobic drugs and hydrophilic polymers to release hydrophilic drugs. The degree of the polymer hydrophobicity/hydrophilicity will dictate the rate of release and the duration of activity.

Polymers useful with this invention include, but are not limited to, polyolefins and their copolymers such as ethylene vinyl acetate, ethylene acrylic acid, ethylene methyl acrylate, plasticized vinyls, polyurethanes, nylons, thermoplastic elastomers such as Hytrel™ and hydrogels. The polymers of choice may or may not be completely crystalline, but preferably have a minimum of 20% amorphous regions. The glass transition temperature of the amorphous regions or amorphous polymers should be less than the body temperature, i.e., less than 35° C.

Suitable matrices for use with the present invention include those disclosed in U.S. Pat. Nos. 4,538,603 and 4,551,490, incorporated by reference herein. A preferred matrix is an ethylene-vinyl acetate copolymer.

The delivery system also includes a means for securing the matrix to the palate or other adequate regions in the oral cavity such as the oral mucosa or tooth. The means for securing the matrix to the oral mucosa may be a thin film/patch that adheres to the palate or other adequate regions in the oral cavity. The securing means also serves as a barrier to prevent penetration of the drug into the mucosa from the matrix, thereby achieving unidirectional delivery of the drug into the oral cavity.

Preferably the securing means is a pressure sensitive adhesive. The pressure sensitive adhesives for securing the matrix to the desired region in the oral cavity must be able to adhere to a moist surface. A preferred pressure sensitive adhesive for use as described herein are the Hydrocolloid pressure sensitive adhesives. Hydrocolloid adhesives are composed of hydrophobic rubbers into which hydrocolloid powders are dispersed (J. L. Chen and G. N. Cyr, Adhesion in Biological Systems, R. S. Manly, ed. p. 163 Academic Press, NY, 1970; incorporated by reference herein). Hydrocolloid adhesives contain from 40 to 60% hydrocolloid powders with the remaining being hydrophobic rubbers. Hydrocolloid powders are materials that exhibit very high water absorption such as gelatin, pectin, polyacrylic acid, sodium carboxymethyl-cellulose, polyethylene oxide, karaya gum, methylcellulose, alginates, hydroxyethyl cellulose and polyvinyl pyrrolidone. Suitable hydrophobic rubbers include, but are not limited to polyisobutylene, butyl rubber, kraton, EPDM (ethylene proplyene diene modified rubber) polyisoprene and hot melt acrylics. Several such systems are described in U.S. Pat. Nos. 3,972,328 and 4,551,490 (incorporated by reference herein).

Non-hydrocolloid adhesives which are substantially hydrophilic to rapidly absorb the moisture from the buccal membrane and provide a dry surface for adhesion to take place may also be used. An example of a non-hydrocolloid adhesive suitable for use as described herein are hydrogels such as those described in U.S. Ser. No. 08/220,530, (filing date: Mar. 30, 1994) and urethane pressure sensitive adhesives described in EP Patent 597636 (incorporated by reference herein).

A preferred means for securing the matrix is an orahesive polymer system such as described in U.S. Pat. No. 3,972,328.

The delivery system of the present invention may optionally contain a barrier membrane. The barrier membrane, when present is located between the matrix for releasing the therapeutic agent and the means for securing the matrix to a region of the oral cavity. The barrier membrane prevents the drug from diffusing from the matrix into the means for securing the matrix. A suitable barrier membrane should be able to adhere to both the matrix and the means for securing and will be able to maintain and/or promote the unidirectional drug delivery into the oral cavity. Suitable barrier membranes for use as described herein are crystalline polymers such as polyesters and or metalized films such as metalized polyethylene or polypropylene. Preferred barrier membranes are coated with very thin tie-layers of polymers which have good adhesion to many polymeric substrates. Such tie-layers include ethylene acrylic acid, ethylene butyl acrylate and ethylene vinyl acetate.

The delivery system may optionally contain a control membrane which is adjacent to the matrix and at the opposite surface from the means for securing. The control membrane is used for better control of the drug release as in the case when the release of the therapeutic agent from the matrix has to be accurately controlled. For example, for very potent drugs or drugs with a narrow therapeutic window. To exert control on drug release, the permeation of the drug through the control membrane has to be slower that through the matrix. Examples of suitable materials for the control membrane are the ethylene vinyl acetate and ethylene methyl acrylate family of copolymers such as those described in U.S. Pat. No. 4,758,434 (incorporated by reference herein) because as the ethylene content of the copolymer is increased, diffusion through the membrane decreases. Thus a particular ratio of ethylene to vinyl acetate can be utilized that would provide the desired control for almost any application. An example of a commercially available ethylene-vinyl acetate copolymer is Vynathene EY904-00/25 from Quantum Chemical Corp., having 51% vinyl acetate content.

Examples of therapeutic agents for use with the present invention are those which have a specific regional absorption i.e., those therapeutic agents which are absorbed from a small section of the gastrointestinal tract or therapeutic agents which have short half-lives. The term "short half-life" or "short half-lives" as used herein refers to half-lives less than 6 (six) hours and preferable less than 3 (three) hours.

An example of a therapeutic agent having a narrow absorption window are angiotensin converting enzyme (ACE) inhibitors such as Captopril (1-[(2s)-3-mercapto-2-methyl-1-oxopropyl]-L-proline), which is absorbed in the duodenum. Captopril is widely used for the treatment of hypertension, heart failure and other cardiovascular conditions. Captopril is generally available in the form of tablets which, as indicated in the Physicians' Desk Reference (PDR) 49th Edition, 1995, page 710, is administered in a dose of from 25 to 150 mg, two or three times daily. Captopril is disclosed in U.S. Pat. No. 4,105,776 to Ondetti et al., the disclosure of which is incorporated by reference herein.

An example of a therapeutic agent useful with this invention, having a short half-life is levodopa. Levodopa is known to be useful in the treatment of Parkinson disease, especially in conjunction with carbidopa. Levodopa in combination with carbidopa is generally available in the form of tablets which, as indicated in the Physicians' Desk reference (PDR) 49th Edition, 1995, pages 959 and 961, are administered in a total of from 200 mg to 1000 mg, in 2 to 4 divided doses daily.

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

A. Matrix Preparation

The matrix for the captopril was an ethylene-vinyl acetate copolymer, Vynathene EY904-00/25 from Quantum Chemical Corp., having 51% vinyl acetate content.

The matrix was prepared by dissolving the ethylenevinyl acetate copolymer in toluene and adding a solution of captopril (100 mg) in methylene chloride. Large volumes of solvent were needed to keep the polymer and drug dissolved due to the hydrophobic nature of the ethylene-vinyl acetate and the hydrophilic nature of captopril. The resulting solution was 16% solids.

A film was prepared by casting the solution in release liner and then carefully removing the solvent in a vacuum oven at room temperature for several hours and gradually raising the temperature with a final drying at 80° C. for two (2) hours. The resulting film was unevenly opaque with some crystallization of captopril on the surface. The film was heat laminated to a Mylar/ethylene-vinyl acetate copolymer backing film at 120° C. for several seconds. Circular disks 3 cm in diameter were punched out and attached to Orahesive with transfer adhesive.

The disk is 3 cm in diameter and approximately 30 mils in thickness. To keep the delivery system a size suitable for use as described, 20 mils thickness was allowed for the captopril matrix. Using these constraints in thickness and area a drug loading of 29% by weight was needed to put 100 mg in the matrix.

What is claimed is:

1. A unidirectional buccal delivery system for the delivery of a therapeutic agent consisting essentially of a matrix, a therapeutic agent contained within said matrix, said matrix being adapted to release said therapeutic agent into the oral cavity at a sustained rate, said therapeutic agent being adapted to be absorbed from a small section of the gastrointestinal tract or has a short half-life of less than 6 hours, and a securing means for securing the matrix to a region of the oral cavity which is the palate, oral mucosa or tooth, whereby upon securing the matrix to a region of the oral cavity, therapeutic agent is released from the matrix into the buccal cavity, away from the securing means, for an extended period of time ranging from about 12 hours to about 7 days.

2. The delivery system of claim 1 wherein the securing means is a pressure sensitive adhesive.

3. The delivery system of claim 2 wherein the pressure sensitive adhesive is a hydrocolloid adhesive.

4. The delivery system of claim 2 wherein the pressure sensitive adhesive is a urethane pressure sensitive adhesive.

5. The delivery system of claim 2 wherein the pressure sensitive adhesive is a hydrogel.

6. The delivery system of claim 1 wherein the matrix for releasing the agent into the oral cavity is ethylene vinyl acetate.

7. The delivery system of claim 1 wherein the matrix for releasing the agent into the oral cavity is polyurethane.

8. The delivery system of claim 1 wherein the matrix for releasing the agent into the oral cavity is a hydrogel.

9. The delivery system of claim 2 wherein the matrix for releasing the agent into the oral cavity is ethylene vinyl acetate, polyurethane or hydrogel.

10. The delivery system of claim (3, 4 or 5) wherein the matrix for releasing the agent into the oral cavity is ethylene vinyl acetate, polyurethane or hydrogel.

11. The delivery system of claim 1 wherein the therapeutic agent is captopril.

12. The delivery system of claim 10 wherein the therapeutic agent is captopril.

13. The delivery system of claim 1 wherein the therapeutic agent is levodopa.

14. The delivery system of claim 11 wherein the captopril is released at a rate of about 0.2 to 20 mg per hr.

* * * * *